United States Patent [19]

Pum et al.

[11] Patent Number: 4,804,705

[45] Date of Patent: Feb. 14, 1989

[54] GEL COMPOSITION

[76] Inventors: Franz Pum, 23417 Covello St., Canoga Park, Calif. 91304; Robert E. Saute, 10236 Mossy Rock Circle, Los Angeles, Calif. 90024

[21] Appl. No.: 90,107

[22] Filed: Aug. 28, 1987

Related U.S. Application Data

[63] Continuation-in-part of Ser. No. 869,345, Jun. 2, 1986, abandoned.

[51] Int. Cl.[4] .................... C08F 299/00; C08G 81/02
[52] U.S. Cl. .................................................. 525/54.21
[58] Field of Search ............................ 524/30, 43, 44; 525/54.21

[56] References Cited

U.S. PATENT DOCUMENTS

| | | | |
|---|---|---|---|
| 3,986,825 | 10/1976 | Sokol | 424/62 |
| 4,128,631 | 12/1978 | Lundmark et al. | 424/70 |
| 4,151,269 | 4/1979 | Torii et al. | 424/47 |
| 4,240,450 | 12/1980 | Grollier et al. | 424/61 |
| 4,299,817 | 11/1981 | Hannon, III et al. | 424/70 |
| 4,445,521 | 5/1984 | Grollier | 424/47 |
| 4,501,834 | 2/1985 | Su | 424/73 |
| 4,517,174 | 5/1985 | Jacquet et al. | 424/62 |
| 4,591,610 | 5/1986 | Grollier | 524/55 |

FOREIGN PATENT DOCUMENTS 864433  2/1971  Canada .

OTHER PUBLICATIONS

New Techniques for Using Carbopol Resins by Lang, Henkel Bulletin on HSP-1180.

National Speciality Chemicals re Celquat Polymers Carbopol Resins, Newsletter No. 6.

*Primary Examiner*—John Kight
*Assistant Examiner*—Nathan M. Nutter
*Attorney, Agent, or Firm*—Kenneth J. Hovet

[57] ABSTRACT

Formation of a stable gel by reacting quaternized hydroxyethyl cellulose with either one or combination of sodium polystyrene sulfonate and polyacrylamidomethylpropane sulfonic acid.

3 Claims, No Drawings

GEL COMPOSITION

This application is a continuation-in-part of copending application Ser. No. 869,345 filed June 2, 1986, now abandoned.

BACKGROUND OF THE INVENTION

FIELD OF THE INVENTION

The present invention relates to gel formulations that have utility as carriers for functional materials.

DESCRIPTION OF THE PRIOR ART

Broadly speaking, a gel is a colloidal solution of a solid in a liquid. Among the more useful gels are those formed with polymers. Xanthan gums, alginates, substituted cellulose derivatives, carboxyvinyl polymers, polyacrylates and polyacrylamides are examples of polymers often used in forming gels.

Disadvantages the above polymers exhibit are that some require a high level of solids to produce a gel, some are sensitive to the presence of even relatively small amounts of electrolytes, some will only form gels over a very narrow pH range and most are temperature dependent.

U.S. Pat. No. 4,501,834 addressed the latter problem by reacting a polysulfonic acid or alginic acid with a quaternized polymer such as poly(diallyldimethylammonium chloride). The gels formed thereby allegedly retain their structure when subjected to unspecified hot and cold temperatures.

Major problems with the above gels concern the requirement of a high level of agitation during reaction. Unless there is intensive mixing, reaction products of the two polymers will precipitate and not form a gel. Further, the presence of extraneous materials such as salts, acids, alkali and anionic or cationic surfactants will destroy the gels and precipitate the polymer complex. Still further, the gels can only be formed over a very narrow concentration which greatly restricts their overall properties and usefulness.

SUMMARY OF THE INVENTION

The invention provides a new gel that does not require a high level of agitation nor is it sensitive to pH, salts, acids, alkali or surfactants. Also, it gives effective workable gels over a wide range of reactant concentration and temperature.

The gel comprises the reaction product from an aqueous solution containing 0.5 to 10.0 weight percent quaternized hydroxyethyl cellulose and 0.1 to 5.0 weight percent of any one or combination of sodium polystyrene sulfonate and polyacrylamidomethylpropane sulfonic acid. When combined, the polyacrylamidomethylpropane sulfonic acid to sodium polystyrene sulfonate weight ratio can range from 0.1/1 to 2.5/1 with a preferred range of 0.3/1 to 2.0/1. The reaction occurs at ambient conditions and requires no extraordinary agitation. Manual stirring in an open vessel is sufficient to produce a clear hydrous gel.

The gel remains stable with the addition of acids and bases over a pH range of 2-14. It is an excellent vehicle for functional materials that do not adversely affect the gel or gel formation. Examples are hair and beauty treatment compositions, cleansing agents such as soaps and synthetic detergents, dyes, pigments, bleaches, abrasives and solvents.

DESCRIPTION OF THE PREFERRED EMBODIMENTS

Polyquaternium-4 or quaternized hydroxyethyl cellulose is manufactured by National Starch and Chemical Corporation under the trademark Celquat. For purposes of this invention, only the most viscous grade, H-100, is effective. It is supplied as a granular powder which is soluble in water.

Polyacrylamidomethylpropane sulfonic acid is provided by Henkel Company under the trademark Cosmedia Polymer HSP-1180. It is described in U.S. Pat. No. 4,128,631 and Canadian Pat. No. 864,433 which are herein incorporated by reference. It is supplied as a thick aqueous solution containing 15 weight percent polymer.

Sodium polystyrene sulfonate is provided by National Starch and Chemical Corporation under the name Flexan 130. It is sold as a 30 weight percent aqueous solution which is how it is utilized in the present invention.

Clear hydrous gels of the invention are produced by initially dissolving the powdered quaternized hydroxyethyl cellulose (hereinafter referenced as H-100) in water to form a 0.5 to 10.0 weight percent solution. Heating the water and mild agitation facilitate solubilization of the powder.

To the above solution is added a 0.1 to 5.0 weight percent aqueous solution of either one or combination of polyacrylamidomethylpropane sulfonic acid (hereinafter referred to as HSP-1180 in the form of a 15 weight percent aqueous solution) and sodium polystyrene sulfonate (hereinafter referred to as F-130 in the form of a 30 weight percent aqueous solution). When combined, the HSP-1180 to F-130 weight ratio ranges from 0.1/1.0 to 2.5/1.0. Gel formation occurs substantially immediately upon the combination of the above polymer(s) with H-100. The reaction occurs under ambient conditions with mild agitation.

It will be appreciated that the gel viscosity is determined by reactant concentration. Therefore, the maximum concentration will be determined primarily by gel viscosity which should not exceed that at which effective mixing of the reactants is possible.

In general, the reaction may be characterized as an ionic interaction between the reactants. Although the gel product is not subject to chemical description, its great stability is believed to significantly result from the strong attraction between the oppositely-charged reactants.

The Examples below illustrate formation of gels within the scope of the present invention.

|  | Part A | Grams | Part B | Grams | Gel Viscosity[1] cps | Wt. Ratio of H-100/ HSP-1180 &/or F-130 | Wt. Ratio HSP-1180 F-130 |
|---|---|---|---|---|---|---|---|
| Ex. 1 | H-100 Water | 2.5 77.5 | HSP-1180 Water | 0.7 17.3 | 45,000 | 3.6/1.0 | — |

-continued

| | Part A | Grams | Part B | Grams | Gel Viscosity[1] cps | Wt. Ratio of H-100/ HSP-1180 &/or F-130 | Wt. Ratio HSP-1180 F-130 |
|---|---|---|---|---|---|---|---|
| Ex. 2 | H-100 | 2.0 | HSP-1180 | 0.5 | 29,500 | 4.0/1.0 | — |
| | Water | 78.0 | Water | 19.5 | | | |
| Ex. 3 | H-100 | 1.5 | HSP-1180 | 0.3 | 11,000 | 5.0/1.0 | — |
| | Water | 78.5 | Water | 19.7 | | | |
| Ex. 4 | H-100 | 1.0 | HSP-1180 | 0.7 | 3,500 | 1.4/1.0 | — |
| | Water | 79.0 | Water | 19.3 | | | |
| Ex. 5 | H-100 | 2.5 | F-130 | 0.5 | 89,000 | 5.0/1.0 | — |
| | Water | 77.5 | Water | 19.5 | | | |
| Ex. 6 | H-100 | 2.0 | F-130 | 0.7 | 90,000 | 2.9/1.0 | — |
| | Water | 78.0 | Water | 19.3 | | | |
| Ex. 7 | H-100 | 1.5 | F-130 | 0.3 | 27,500 | 5.0/1.0 | — |
| | Water | 78.5 | Water | 19.7 | | | |
| Ex. 8 | H-100 | 1.0 | F-130 | 0.7 | 15,000 | 1.4/1.0 | — |
| | Water | 77.0 | Water | 14.3 | | | |
| Ex. 9 | H-100 | 2.5 | HSP-1180 | 0.5 | 215,000 | 3.1/1.0 | 1.7/1.0 |
| | Water | 77.0 | F-130 | 0.3 | | | |
| | | | Water | 19.2 | | | |
| Ex. 10 | H-100 | 2.0 | HSP-1180 | 0.7 | 205,000 | 1.7/1.0 | 1.4/1.0 |
| | Water | 78.0 | F-130 | 0.5 | | | |
| | | | Water | 18.8 | | | |
| Ex. 11 | H-100 | 1.5 | HSP-1180 | 0.3 | 115,000 | 1.5/1.0 | 0.4/1.0 |
| | Water | 78.5 | F-130 | 0.7 | | | |
| | | | Water | 19.0 | | | |
| Ex. 12 | H-100 | 1.0 | HSP-1180 | 0.5 | 28,000 | 1.0/1.0 | 1.0/1.0 |
| | Water | 79.0 | F-130 | 0.5 | | | |
| | | | Water | 19.0 | | | |
| Ex. 13 | H-100 | 1.0 | HSP-1180 | 0.1 | 14,000 | 10.0/1.0 | — |
| | Water | | Water | 98.9 | | | |
| Ex. 14 | H-100 | 1.0 | HSP-1180 | 0.5 | 44,000 | 2.0/1.0 | — |
| | Water | | Water | 98.5 | | | |
| Ex. 15 | H-100 | 1.0 | HSP-1180 | 1.0 | 84,000 | 1.0/1.0 | — |
| | Water | | Water | 98.0 | | | |
| Ex. 16 | H-100 | 1.0 | HSP-1180 | 1.5 | 60,000 | 0.7/1.0 | — |
| | Water | | Water | 97.5 | | | |
| Ex. 17 | H-100 | 1.0 | HSP-1180 | 2.0 | 75,000 | 0.5/1.0 | — |
| | Water | | Water | 97.0 | | | |
| Ex. 18 | H-100 | 1.0 | HSP-1180 | 2.5 | 80,000 | 0.4/1.0 | — |
| | Water | | Water | 96.5 | | | |
| Ex. 19 | H-100 | 1.0 | F-130 | 0.1 | 37,000 | 10.0/1.0 | — |
| | Water | | Water | 98.9 | | | |
| Ex. 20 | H-100 | 1.0 | F-130 | 0.5 | 23,000 | 2.0/1.0 | — |
| | Water | | Water | 98.5 | | | |
| Ex. 21 | H-100 | 1.0 | F-130 | 1.0 | 26,000 | 1.0/1.0 | — |
| | Water | | Water | 98.0 | | | |
| Ex. 22 | H-100 | 1.0 | F-130 | 1.5 | 27,000 | 0.7/1.0 | — |
| | Water | | Water | 97.5 | | | |
| Ex. 23 | H-100 | 1.0 | F-130 | 2.0 | 28,500 | 0.5/1.0 | — |
| | Water | | Water | 97.0 | | | |
| Ex. 24 | H-100 | 1.0 | F-130 | 2.5 | 25,000 | 0.4/1.0 | — |
| | Water | | Water | 96.5 | | | |
| Ex. 25 | H-100 | 1.0 | HSP-1180 | 0.05 | 17,500 | 10.0/1.0 | 1.0/1.0 |
| | Water | | F-130 | 0.05 | | | |
| | | | Water | 98.9 | | | |
| Ex. 26 | H-100 | 1.0 | HSP-1180 | 0.1 | 45,000 | 5.0/1.0 | 1.0/1.0 |
| | Water | | F-130 | 0.1 | | | |
| | | | Water | 98.8 | | | |
| Ex. 27 | H-100 | 1.0 | HSP-1180 | 0.25 | 27,500 | 2.0/1.0 | 1.0/1.0 |
| | Water | | F-130 | 0.25 | | | |
| | | | Water | 98.5 | | | |
| Ex. 28 | H-100 | 1.0 | HSP-1180 | 0.5 | 26,000 | 1.0/1.0 | 1.0/1.0 |
| | Water | | F-130 | 0.5 | | | |
| | | | Water | 98.0 | | | |
| Ex. 29 | H-100 | 1.0 | HSP-1180 | 0.75 | 15,000 | 0.7/1.0 | 1.0/1.0 |
| | Water | | F-130 | 0.75 | | | |
| | | | Water | 97.5 | | | |
| Ex. 30 | H-100 | 1.0 | HSP-1180 | 1.0 | 14,000 | 0.5/1.0 | 1.0/1.0 |
| | Water | | F-130 | 1.0 | | | |
| | | | Water | 97.0 | | | |
| Ex. 31 | H-100 | 1.0 | HSP-1180 | 1.25 | 21,000 | 0.4/1.0 | 1.0/1.0 |
| | Water | | F-130 | 1.25 | | | |
| | | | Water | 96.5 | | | |

[1]Brookfield Viscometer Model RVF, Spindle TB @ 4 rpm & 24° C.

The reaction procedure for the above Examples was to combine Part A and dissolve the H-100 powder with mold agitation. Warming to 55° C. helps dissolution. Part B was combined with stirring and then added to Part A, also with stirring. In each Example, a clear gel was formed.

Each of the above gels was heated to near boiling and then cooled. The original viscosity and clear appearance were unaltered. Identical results were obtained when the gels were tested at near freezing temperatures.

Because the gels have great stability over a wide range of conditions and diluency, their utility as vehicles for a large number of functional materials is significant. By "functional", it is meant that the material or ingredient has separate or independent utility. Such materials must be noninterfering with gel formation and stability and they should not react with the gel-forming polymers.

The functional materials are preferably added to either of the initial polymer solutions prior to reaction. This avoids any difficulty that may arise in dispersing the materials after a stiff gel is formed. Most conveniently, the materials are added to the initial H-100 solution since this has the greater volume.

The Table below sets forth a variety of illustrative functional ingredients or material categories that may be added alone or in combination to the gel product or initial polymer reactant solutions. Since the ingredients are noninterfering with the polymer reaction, i.e., gel formation and subsequent stability, the suggested weight percent ranges do not necessarily represent upper and lower limits. They do represent useful and effective concentrations.

TABLE

| Material | Use | Weight Percent Range of Overall Composition |
| --- | --- | --- |
| Magnesium sulfate-2H$_2$O | Hair Conditioning | 3–10 |
| Ammonium thioglycolate (60%) | Permanent Hair Wave | 7–12 |
| Hydrogen Peroxide (50%) | Hair Bleaching | 1–24 |
| Dyes | Hair Coloring | 0.0001–5 |
| Dye Intermediates | Hair Dying | 0.0001–5 |
| Surfactants | Hair Shampoo | 1–40 |
| Solvents and Detergents | Substrate Cleaners and Paint Removers | 1–50 |
| Oxalic Acid | Rust Remover | 2–10 |
| Surfactants and Pumice | Skin Cleaning and Buffing | 1–20 |
| Iron Oxide, Rotstone | Polishing | 2–10 |
|  |  | 1–10 |

The following are examples illustrating initial polymer compositions in combination with representative functional materials at effective concentrations. The procedure in each of the following examples for combining the materials is the same as with Examples 1–31. In each example, a stable gel was formed that enhanced effective use of the functional materials contained therein.

| | Part A | Grams | Part B | Grams | Gel Product |
| --- | --- | --- | --- | --- | --- |
| Example 32 | H-100<br>Water<br>Magnesium Sulfate 2H$_2$O | 2.00<br>70.00<br>10.00 | HSP-1180<br>Water | 0.50<br>17.50 | Hair Conditioner |
| Example 33 | H-100<br>Water<br>Ammonium thioglycolate (60% aqueous)<br>Ammonia (28% aqueous) | 1.70<br>67.2<br>11.60<br>3.00 | F-130<br>Water | 0.40<br>16.50 | Permanent Hair Waving Solution |
| Example 34 | H-100<br>Water<br>Hydrogen Peroxide (50% aqueous)<br>pH was adjusted to 3.6 with 10% triethanolamine soln. | 2.00<br>85.50<br>12.00 | HSP-1180 | 0.50 | Hair Bleaching |
| Example 35 | H-100<br>Water<br>Oxalic Acid | 2.00<br>92.50<br>5.00 | HSP-1180 | 0.50 | Rust Remover |
| Example 36 | H-100<br>Water<br>Insoluble Pigment | 1.50<br>93.20<br>5.00 | Flexan-130 | 0.30 | Cosmetic Coloring |
| Example 37 | H-100<br>Water<br>Soluble Dye | 2.00<br>96.30<br>1.00 | HSP-1180 | 0.70 | Hair Dying |

While the invention has been described with reference to specific illustrative embodiments, it will be apparent that various changes can be made without departing from the scope and spirit of the invention as hereinafter set forth in the claims.

We claim:

1. A gel formed with mild agitation by the reaction product of an aqueous solution consisting of 0.5 to 10.0 weight percent quaternized hydroxyethyl cellulose and 0.1 to 5.0 weight percent of an aqueous solution consisting of polyacrylamidomethylpropane sulfonic acid and sodium polystyrene sulfonate which are combined in a weight ratio ranging from 0.1/1.0 to 2.5/1.0 polyacrylamidomethylpropane sulfonic acid to sodium polystyrene sulfonate.

2. A hydrous gel formed with mild agitation consisting of the reaction product of an aqueous solution containing of 0.5 to 10.0 weight percent quaternized hydroxyethyl cellulose and 0.1 to 5.0 weight percent of polyacrlylamidomethylpropane sulfonic acid.

3. A hydrous gel formed with mild agitation consisting of the reaction product of an aqueous solution containing 0.5 to 10.0 weight percent quaternized hydroxyethyl cellulose and 0.1 to 5.0 weight percent sodium polystyrene sulfonate.

* * * * *